United States Patent [19]

Campbell et al.

[11] Patent Number: 4,740,513
[45] Date of Patent: Apr. 26, 1988

[54] METHYL SUBSTITUTED IMIDAZOL-1-YL QUINOLONES

[75] Inventors: Simon F. Campbell; David A. Roberts, both of Deal, England

[73] Assignee: Pfizer Inc., New York, N.Y.

[21] Appl. No.: 929,456

[22] Filed: Nov. 12, 1986

[30] Foreign Application Priority Data

Nov. 28, 1985 [GB] United Kingdom ............... 8529362

[51] Int. Cl.$^4$ ................... C07D 401/04; A61K 31/47
[52] U.S. Cl. .................................. 514/312; 546/157; 548/337; 548/341
[58] Field of Search .............. 514/312; 546/157, 158

[56] References Cited

U.S. PATENT DOCUMENTS

| | | | |
|---|---|---|---|
| 3,993,656 | 11/1976 | Rooney et al. | 546/122 |
| 4,258,185 | 3/1981 | Nakao et al. | 544/114 |
| 4,277,479 | 7/1981 | Nishi et al. | 546/157 |
| 4,284,787 | 8/1981 | Knupper et al. | 548/256 |

FOREIGN PATENT DOCUMENTS

| | | |
|---|---|---|
| 0052016 | 5/1982 | European Pat. Off. |
| 0102046 | 3/1984 | European Pat. Off. |
| 0155798 | 9/1985 | European Pat. OFf. |
| 54-73783 | 6/1979 | Japan . |
| 55-76872 | 6/1980 | Japan ................. 514/312 |
| WO85/02402 | 6/1985 | PCT Int'l Appl. |
| 2086896 | 5/1982 | United Kingdom . |
| 2127402 | 4/1984 | United Kingdom . |
| 2147581 | 5/1985 | United Kingdom . |

OTHER PUBLICATIONS

Tominaga et al. English Abstract for WO82/01706 (5/27/82).

*Primary Examiner*—Donald G. Daus
*Assistant Examiner*—E. Bernhardt
*Attorney, Agent, or Firm*—Peter C. Richardson; Lawrence C. Akers; J. Trevor Lumb

[57] ABSTRACT

A series of novel heterocyclic-substituted 2-(1H)-quinolone compounds have been prepared wherein the heterocyclic ring moiety is a substituted pyrrolyl, imidazolyl, pyrazolyl, triazolyl or tetrazolyl group attached by a nitrogen atom of said group to the 5-, 6-, 7- or 8-positions of the quinolone ring. These particular compounds are useful in therapy as highly potent cardiac stimulants and therefore, are of value in the treatment of various cardiac conditions. Typical member compounds include those 6-(heterocyclic-substituted)-8-methyl-2-(1H)-quinolones wherein the heterocyclic ring moiety is a ring-substituted imidazol-1-yl group and preferably, an imidazol-1-yl group substituted with one or two methyl groups and a monoacetyl group. 6-(4-Acetyl-2-methylimidazol-1-yl)-8-methyl--2-(1H)-quinolone represents a typical and preferred member compound. Methods for preparing all these compounds from known starting materials are provided.

7 Claims, No Drawings

METHYL SUBSTITUTED IMIDAZOL-1-YL QUINOLONES

Although the compounds of the formula (I) are written as 2-(1H)-quinolones, it should be realised that the following tautomerism can occur:

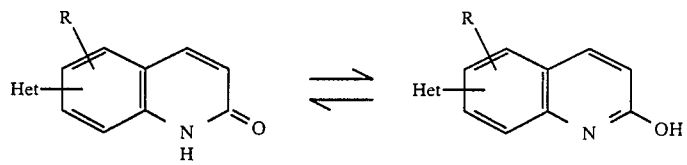

BACKGROUND OF THE INVENTION

This invention relates to substituted quinolone cardiac stimulants which in general selectively increase the force of myocardial contraction without producing a significant increase in the heart rate. The compounds are useful in the curative or prophylactic treatment of cardiac conditions, in particular in the treatment of heart failure.

SUMMARY OF THE INVENTION

Thus according to the invention there are provided substituted 2-(1H)-quinolones of the formula:

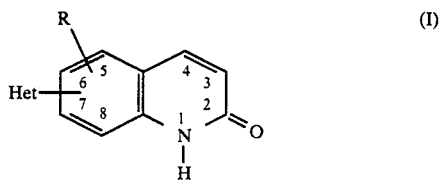

and their pharmaceutically acceptable salts,
wherein
"Het" is a 5-membered monocyclic aromatic heterocyclic group containing at least one nitrogen atom in the aromatic ring and attached by a nitrogen atom to the 5-, 6-, 7- or 8-position of the quinolone;
"Het" being substituted by a group selected from

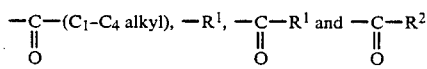

wherein $R^1$ is a phenyl group optionally substituted by 1 to 3 substituents each independently selected from $C_1$-$C_4$ alkyl, $C_1$-$C_4$ alkoxy, hydroxy, halo, trifluoromethyl, $-CONR^3R^4$, $-SO_2NR^3R^4$, $-N(R^3-)SO_2(C_1$-$C_4$ alkyl) and $-S(O)_n(C_1$-$C_4$ alkyl) where $R^3$ and $R^4$ are each H or $C_1$-$C_4$ alkyl and n is 0, 1 or 2, and $R^2$ is a heterocyclic group selected from thienyl, furyl, imidazolyl, triazolyl and tetrazolyl, said heterocyclic group being attached to the adjacent carbonyl group by a ring carbon atom and being optionally substituted by up to two substituents each independently selected from $C_1$-$C_4$ alkyl, $C_1$-$C_4$ alkoxy and halo;
"Het" also being optionally substituted by up to two $C_1$-$C_4$ alkyl groups;
and R, which is attached to the 5-, 6-, 7- or 8-position of the quinolone, is H, $C_1$-$C_4$ alkyl, $C_1$-$C_4$ alkoxy, hydroxy, $CF_3$, halo, cyano or hydroxymethyl.

"Halo" means F, Cl, Br or I. $C_3$ and $C_4$ alkyl and alkoxy groups can be straight or branched chain. The preferred alkyl and alkoxy groups are methyl and methoxy.

However, as the keto-form is considered the more stable tautomer, the end products herein will be named and illustrated as quinolones although those skilled in the art will realise that both tautomers may be present or that any particular compound so named may exist predominantly as the hydroxy tautomer and the following disclosure is to be interpreted to incorporate all tautomeric forms.

Preferably, "Het" contains 1, 2, 3 or 4 nitrogen atoms (and no other heteroatoms) in the aromatic ring.

Examples of said group "Het" are pyrrolyl, imidazolyl, pyrazolyl, triazolyl and tetrazolyl, all substituted as defined for formula (I). "Het" is preferably a 1-imidazolyl group substituted as defined for formula (I).

"Het" is preferably attached to the 6-position of the quinolone.

R is preferably attached to the 8-position.

R is preferably H, $C_1$-$C_4$ alkyl, $CF_3$ or halo. More preferably R is H, $CH_3$, $CF_3$ or Br. R is most preferably $CH_3$.

One group of compounds of the present invention of particular interest is that of structural formula (I) wherein "Het" is attached to the 6-position of the quinolone ring and is a pyrrolyl, imidazol-1-yl, pyrazolyl, triazolyl or tetrazolyl group substituted with (a) one or two methyl groups and (b) a monosubstituent selected from $-CO(C_1$-$C_4$ alkyl), $-COR^1$, $-COR^2$ and $-R^1$ wherein $R^1$ is a phenyl group optionally substituted with one or two substituents each selected from $C_1$-$C_4$ alkyl, $C_1$-$C_4$ alkoxy, hydroxy, halo, trifluoromethyl, $-NHSO_2(C_1$-$C_4$ alkyl), $-S(C_1$-$C_4$ alkyl), $-SO(C_1$-$C_4$ alkyl) and $-SO_2(C_1$-$C_4$ alkyl), and $R^2$ is a triazolyl group attached by a ring carbon atom of said group to the adjacent carbonyl group, said triazolyl group being optionally substituted with a $C_1$-$C_4$ alkyl group. Preferred compounds within this group include those where "Het" is defined as aforesaid, and R is attached to the 8-position of the quinolone ring and is hydrogen, methyl, trifluoromethyl or bromo. A particularly preferred group of compounds within this category are compounds where "Het" is a pyrrolyl, imidazol-1-yl, pyrazolyl, triazolyl or tetrazolyl group substituted with one or two methyl groups and a monoacetyl group, and R is as defined above but is preferably a methyl group.

The most preferred individual compounds of the formula (I) have the formula:

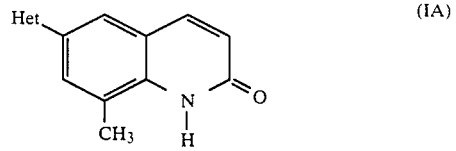

where Het is as defined for formula (I), and is preferably a 1-imidazolyl group substituted as defined for formula (I).

In the quinolones of the formulae (I) and (IA), "Het" is more preferably an imidazol-1-yl group substitued by (a) one or two methyl groups and (b) a group of the formula —CO($C_1$-$C_4$ alkyl), —$R^1$, —$COR^1$ or —$COR^2$ where $R^1$ is a phenyl group optionally substituted by 1 or 2 substituents each selected from $C_1$-$C_4$ alkyl, $C_1$-$C_4$ alkoxy, hydroxy, halo, —$CF_3$, $C_1$-$C_4$ alkylthio, $C_1$-$C_4$ alkylsulphinyl, $C_1$-$C_4$ alkylsulphonyl and —$NHSO_2$(-$C_1$-$C_4$ alkyl), and $R^2$ is a triazolyl group optionally substituted by a $C_1$-$C_4$ alkyl group.

Most preferably, "Het" is an imidazol-1-yl group substituted by an acetyl group and by one or two methyl groups.

The most preferred compound is 6-(4-acetyl-2-methylimidazol-1-yl)-8-methyl-2-(1H)-quinolone.

The pharmaceutically acceptable salts of the compounds of the formula (I) are either addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, methanesulphonate and p-toluenesulphonate salts, or are metal salts, particularly the alkaline earth or alkali metal salts. The preferred metal salts are the sodium and potassium salts. All the salts are preparable by conventional techniques.

The cardiac stimulant activity of the compounds of the formula (I) is shown by their effectiveness in one or more of the following tests: (a) increasing the force of contraction in the "Starling" dog heart-lung preparation measured via a left ventricular catheter; (b) increasing myocardial contractility (left ventricular dp/dt max.) in the anaesthetised dog measured via a left ventricular catheter; (c) increasing myocardial contractility in the conscious dog with an implanted left ventricular transducer (dp/dt max.) or an exteriorised carotid artery loop (systolic time intervals).

In test (a), the positive inotropic effect of the test compound following bolus administration is measured in the "Starling" dog heart-lung preparation. The selectivity for increase in force versus frequency of contraction of the test compound is obtained.

In test (b), the positive inotropic action of the test compound following intravenous administration is measured in the anaesthetised dog. The magnitude and duration of this action, and the selectivity for increase in force versus frequency of contraction of the test compound are obtained, as are the peripheral effects, e.g. the effect on blood pressure.

In test (c) the positive inotropic action of the test compound following intravenous or oral administration to a conscious dog with an implanted left ventricular transducer (dp/dt max.) or an exteriorised carotid artery loop (systolic time intervals) is measured. The magnitude of the inotropic action, the selectivity for increase in force versus frequency of contraction, and the duration of action of the inotropic effect of the test compound are all obtained.

The compounds of the formula (I) can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, it is expected that oral dosages of the compounds of the invention will be in the range from 1 mg to 250 mg daily, taken in 1 to 3 divided doses per day, for an average adult patient (70 kg). Dosages for intravenous administration would be expected to be within the range 0.1 to 100 mg per single dose as required, for example in the treatment of acute heart failure. Thus for a typical adult patient, individual tablets or capsules might contain 0.1 to 100 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of stimulating the heart of a human being, which comprises administering to said human a compound of formula (I) or pharmaceutically acceptable salt thereof, or a pharmaceutical composition as defined above, in an amount sufficient to stimulate the heart of said human.

The invention yet further provides a compound of the formula (I) or pharmaceutically acceptable salt thereof, for use as a medicament, in particular for use in stimulating the heart of a human being suffering from congestive heart failure.

The invention yet further provides the use of a compound of the formula (I), or of a pharmaceutically acceptable salt thereof, for the manufacture of a medicament for use as a cardiac stimulant.

DETAILED DESCRIPTION OF THE INVENTION

The compounds of formula (I) can be prepared by a number of routes, including the following:

Route A:

This method is illustrated as follows:

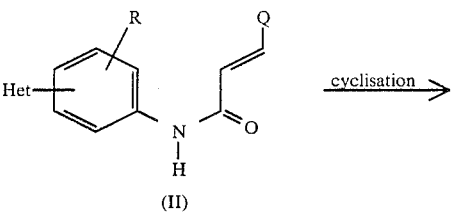

-continued

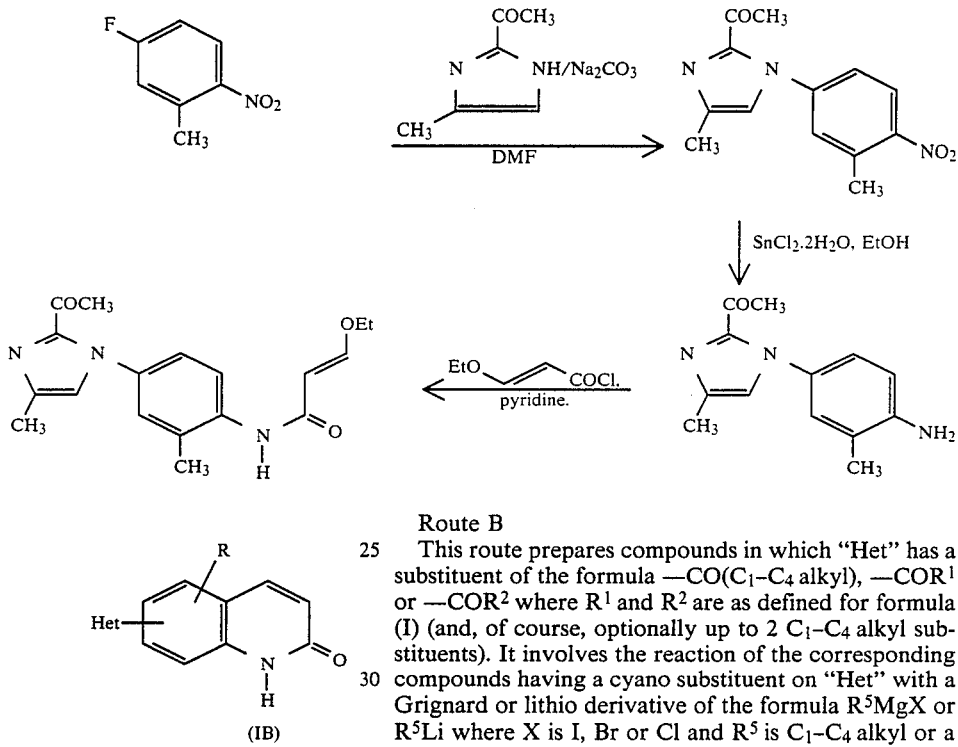

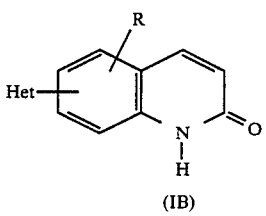

The novel intermediates (II) also form a part of the invention.

Het and R are as defined for formula (I) and Q is a leaving group such as $C_1$–$C_4$ alkoxy, preferably ethoxy or methoxy. The cyclisation is preferably carried out by treating the propenamide derivative (II) with concentrated, desirably substantially anhydrous (98%), sulphuric acid at room temperature until the reaction is complete, typically in 6–48 hours. If necessary, heating at up to 100° C. can be carried out to accelerate the reaction. The product can then be isolated and purified by conventional procedures.

The propenamide (II) can also be used in acid addition salt form (e.g. as a hydrochloride).

A typical reaction is illustrated as follows:

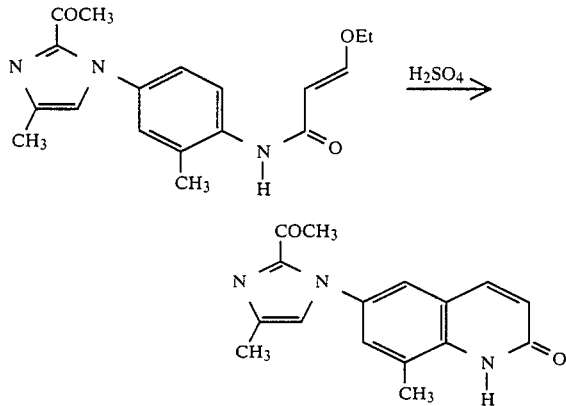

The starting materials of the formula (II) can be prepared by conventional procedures. A typical route, which is illustrated in detail in the following Preparations, is as follows:

Route B

This route prepares compounds in which "Het" has a substituent of the formula —CO($C_1$–$C_4$ alkyl), —COR$^1$ or —COR$^2$ where R$^1$ and R$^2$ are as defined for formula (I) (and, of course, optionally up to 2 $C_1$–$C_4$ alkyl substituents). It involves the reaction of the corresponding compounds having a cyano substituent on "Het" with a Grignard or lithio derivative of the formula R$^5$MgX or R$^5$Li where X is I, Br or Cl and R$^5$ is $C_1$–$C_4$ alkyl or a group of the formula R$^1$ or R$^2$, followed by treatment with an aqueous acid, preferably an aqueous mineral acid such as hydrochloric acid. It is preferred to use a Grignard reagent of the formula R$^5$MgBr.

The reaction is typically carried out by heating the starting cyano-substituted compound with the Grignard or lithio reagent in a suitable organic solvent, e.g. tetrahydrofuran, at up to the reflux temperature, generally for 1–6 hours, followed by stirring with the acid, typically at room temperature for a short period. The product can then be isolated and purified by conventional means.

A typical reaction is illustrated as follows:

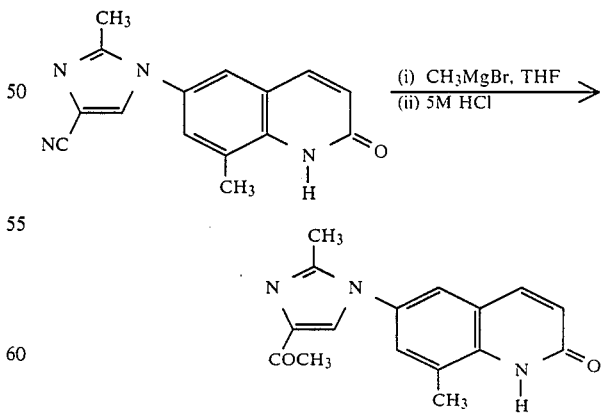

The cyano-containing starting materials can be prepared by conventional procedures such are as described in the following Preparations (see also European patent application publication No. 0166533). A typical route is as follows:

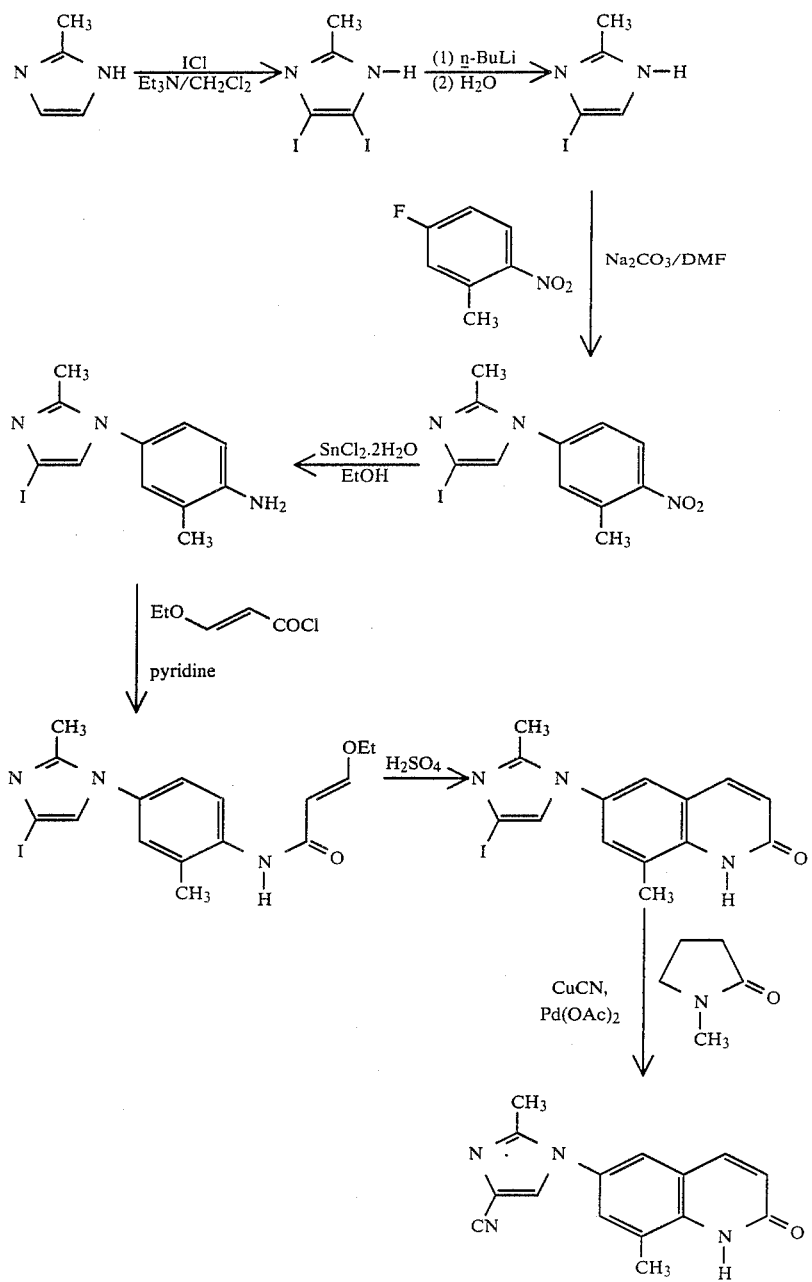

Route C

This route prepares compounds in which "Het" has a substituent of the formula $R^1$ where $R^1$ is as defined for formula (I) (and, of course, optionally up to two $C_1$-$C_4$ alkyl groups), and involves the reaction of the corresponding compound having a bromo- or iodo-substituent on "Het" with an aryl zinc halide of the formula $R^1$—Zn—X where X is I, Br or Cl. The reaction is desirably carried out in the presence of a palladium (O) catalyst. X is preferably Cl. Also, it is preferred to use a starting material having an iodo substituent on "Het".

The reaction is typically carried out by heating the bromo- or iodo-substituted starting material with the aryl zinc halide in the presence of a palladium catalyst, preferably tetrakis(triphenylphosphine)palladium (O), and in a suitable organic solvent, e.g. tetrahydrofuran, at up to the reflux temperature, generally for 1–24 hours. The product can then be isolated and purified by conventional means.

Typical reactions of this type are illustrated as follows:

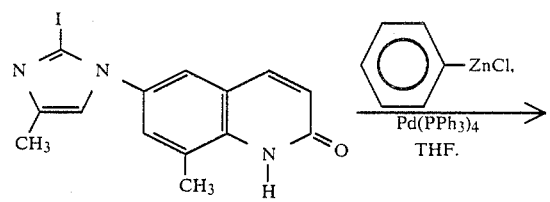

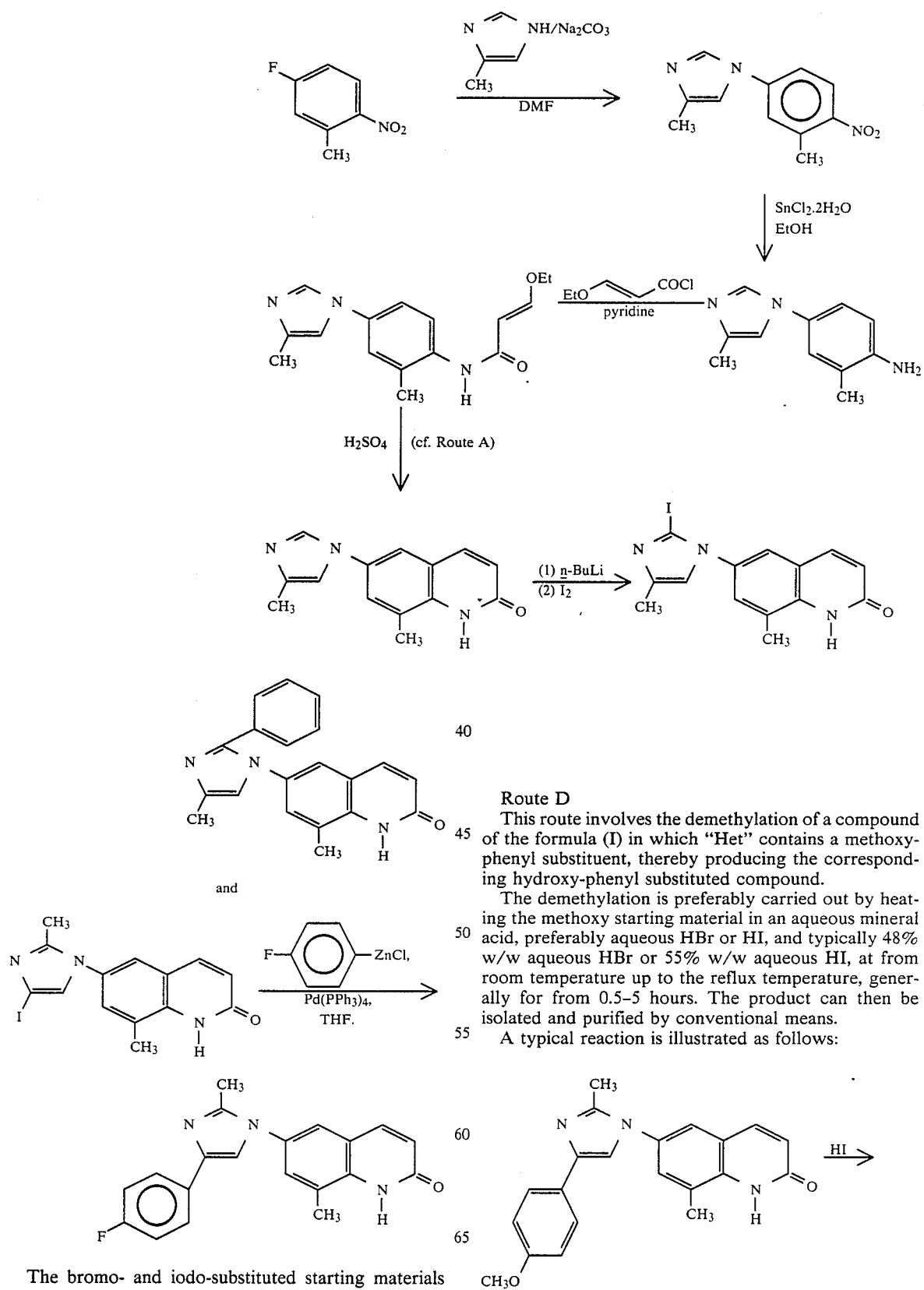

European patent application publication No. 0166533). A typical route is illustrated as follows:

The bromo- and iodo-substituted starting materials can be prepared by conventional procedures (see e.g.

Route D

This route involves the demethylation of a compound of the formula (I) in which "Het" contains a methoxy-phenyl substituent, thereby producing the corresponding hydroxy-phenyl substituted compound.

The demethylation is preferably carried out by heating the methoxy starting material in an aqueous mineral acid, preferably aqueous HBr or HI, and typically 48% w/w aqueous HBr or 55% w/w aqueous HI, at from room temperature up to the reflux temperature, generally for from 0.5-5 hours. The product can then be isolated and purified by conventional means.

A typical reaction is illustrated as follows:

-continued

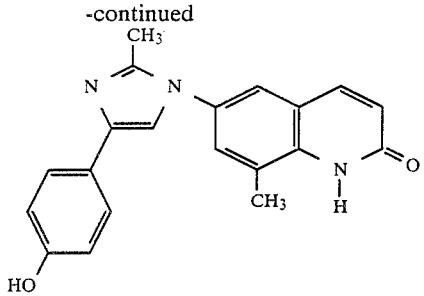

The methoxy-starting materials are prepared by conventional procedures, typically by the method outlined in Route C above.

Route E

This route prepares compounds in which "Het" has a $C_1$-$C_4$ alkylsulphinyl-phenyl substituent, and involves the reaction of the corresponding compound having a $C_1$-$C_4$ alkylthio-phenyl substituent with a suitable oxidising agent, e.g. m-chloroperbenzoic acid or hydrogen peroxide.

The reaction is typically carried out by stirring the alkylthio-substituted starting material with meta-chloroperbenzoic acid (m-CPBA) in a suitable organic solvent, e.g. dichloromethane, at 0° C., generally for 0.5–3 hours. The product can then be isolated and purified by conventional means.

A typical reaction of this type is illustrated as follows:

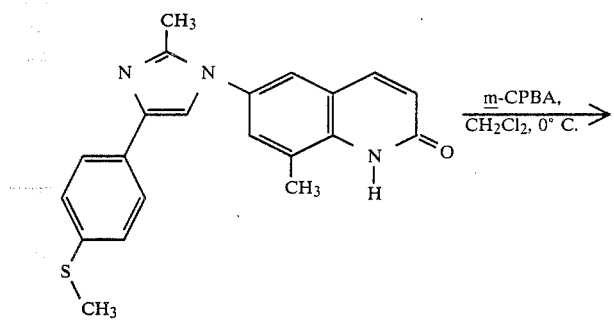

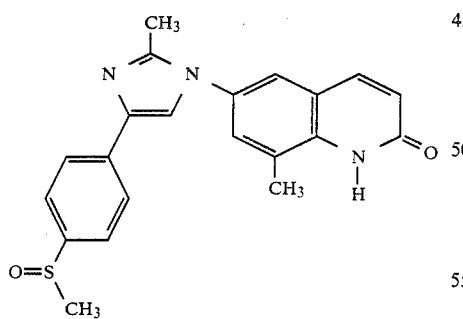

Route F

This route prepares compounds in which "Het" has a $C_1$-$C_4$ alkylsulphonyl-phenyl substituent, and involves the reaction of the corresponding compound having a $C_1$-$C_4$ alkylsulphinyl-phenyl substituent with a suitable oxidising agent, e.g. m-chloroperbenzoic acid or hydrogen peroxide.

The reaction is typically carried out by stirring the alkylsulphinyl-substituted starting material with meta-chloroperbenzoic acid in a suitable organic solvent, e.g. dichloromethane, at up to 30° C., generally for 0.5–3 hours. The product can then be isolated and purified by conventional means.

A typical reaction of this type is illustrated as follows:

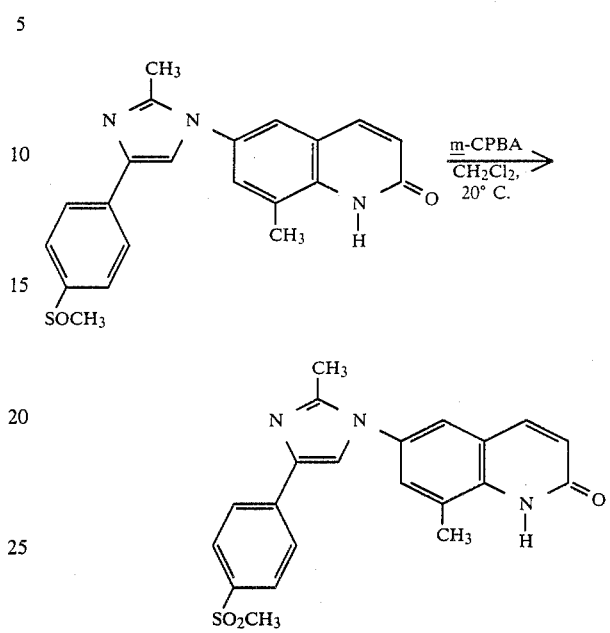

Alternatively, compounds in which $R^1$ is a phenyl group substituted by a $C_1$-$C_4$ alkylsulphonyl group (and, of course, optionally by up to two $C_1$-$C_4$ alkyl groups) can be prepared by the direct oxidation of the corresponding $C_1$-$C_4$ alkylthio derivatives using an excess (at least two equivalents) of the oxidising agent.

Route G

The compounds of the formula (I) can also be prepared by the Goldberg reaction, as follows:

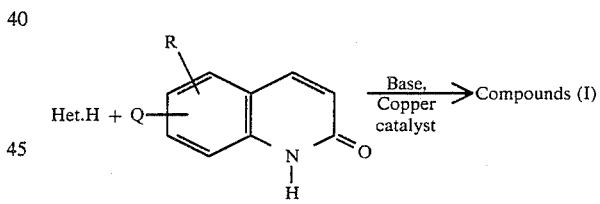

Q is a leaving group such as Cl, Br or I. Q is preferably Br or I. The reaction is carried out in the presence of a copper catalyst, preferably a copper (O) catalyst such as finely divided copper-bronze. Potassium carbonate is a useful base. A typical reaction involves the reaction of the bromo-quinolone with the heterocycle in the presence of copper-bronze, potassium carbonate and iodine with heating at up to about 200° C. in a suitable organic solvent, eg., N-methyl-2-pyrrolidone. The product can then be isolated and purified conventionally.

The quinolone starting materials are either known compounds (see European patent application publication No. 0148623) or can be prepared by conventional techniques.

Where the compounds of the invention contain one or more asymmetric centres, then the invention includes the separated enantiomers and diastereoisomers or mixtures thereof. The separated forms can be obtained by conventional means.

The following Examples illustrate the invention (all temperatures are in °C.):

EXAMPLE 1

Preparation of 6-(2-acetyl-4-methylimidazol-1-yl)-8-methyl-2-(1H)-quinolone, 0.25H₂O

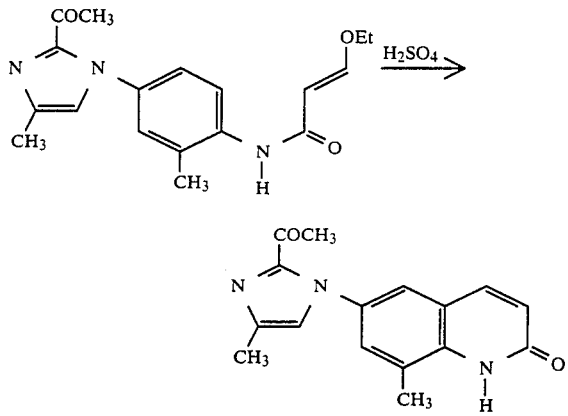

Trans-1-{4-[N-(3-ethoxypropenamido)]-3-methylphenyl}-2-acetyl-4-methylimidazole (0.33 g) was added with stirring to 98% w/w sulphuric acid (1 cm³) at 0°. After 24 hours at room temperature (20°) the mixture was poured carefully onto ice (20 g) and the resulting solution was basified to pH 8 with saturated aqueous sodium bicarbonate. The mixture was then extracted with dichloromethane (3×100 cm³), and the combined and dried (MgSO₄) organic extracts were evaporated in vacuo to give a solid which was recrystallised from ethyl acetate/methanol to afford the title compound, m.p. 312°–314° (0.13 g).

Analysis %: Found: C, 67.3; H, 5.5; N, 14.5; Calculated for $C_{16}H_{15}N_3O_2 \cdot 0.25H_2O$: C, 67.3; H, 5.4; N, 14.7.

EXAMPLE 2

Preparation of 6-(5-acetyl-2,4-dimethylimidazol-1-yl)-8-methyl-2-(1H)-quinolone

This compound, m.p. 240°–242°, was prepared similarly to Example 1 from the appropriately substituted propenamide derivative and 98% H₂SO₄.

Analysis %: Found: C, 69.0; H, 5.8; N, 14.4; Calculated for $C_{17}H_{17}N_3O_2$: C, 69.2; H, 5.8; N, 14.2.

EXAMPLE 3

Preparation of 6-(4-acetyl-2-methylimidazol-1-yl)-8-methyl-2-(1H)-quinolone, 0.17H₂O

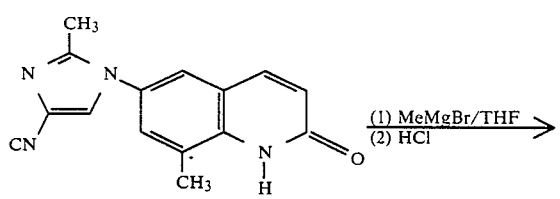

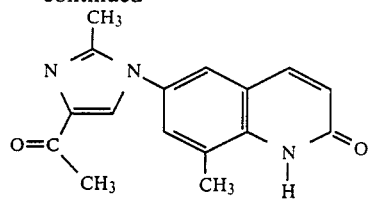

Methyl magnesium bromide (1.11 cm³ of a 3M solution in diethyl ether) was added dropwise to a stirred solution of 6-(4-cyano-2-methylimidazol-1-yl)-8-methyl-2-(1H)-quinolone (0.15 g) in tetrahydrofuran (THF) (25 cm³) at 0° under nitrogen. The mixture was heated under reflux for 2 hours, cooled to room temperature, quenched with water (10 cm³) and then stirred for 30 minutes with 5M hydrochloric acid (10 cm³). The mixture was basified with 10% sodium carbonate solution and extracted with dichloromethane (3×100 cm³). The combined and dried (MgSO₄) organic extracts were evaporated in vacuo to give a solid which was chromatographed on silica (Merck "MK 60.9385" [Trade Mark]). Elution with methanol:dichloromethane, 1:19 by volume, followed by combination and evaporation of appropriate fractions gave a solid which was recrystallised from ethyl acetate-methanol to afford the title compound, m.p. 306°–308° (0.05 g).

Analysis %: Found: C, 67.4; H, 5.4; N, 14.8; Calculated for $C_{16}H_{15}N_3O_2 \cdot 0.17H_2O$: C, 67.6; H, 5.4; N, 14.8.

EXAMPLES 4–8

The following compounds (formula IC) were prepared similarly to the procedure of Example 3 using the appropriate Grignard reagent of the formula R⁵MgBr and 6-(4-cyano-2-methylimidazol-1-yl)-8-methyl-2-(1H)-quinolone as the starting materials:

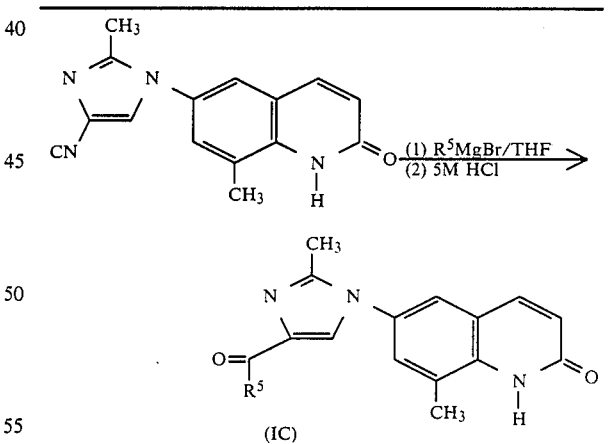

| Example No. | R⁵ | Form Isolated and m.p. (°C.) | Analysis % (Theoretical in brackets) | | |
|---|---|---|---|---|---|
| | | | C | H | N |
| 4 | —C₂H₅ | Free base, 261–3° | 69.0 (69.2 | 5.9 5.8 | 13.7 14.2) |
| 5 | —CH(CH₃)₂ | Free base 0.17 H₂O, 224–7° | 69.3 (69.2 | 6.3 6.2 | 13.2 13.5) |
| 6 | —⌬ | Free base 0.5 H₂O, 290–3° | 71.4 (71.6 | 4.9 5.1 | 11.7 11.9) |

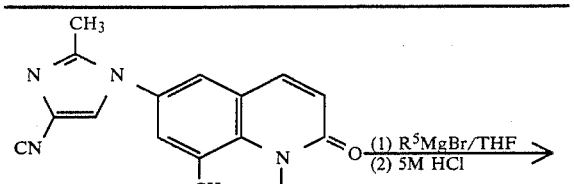

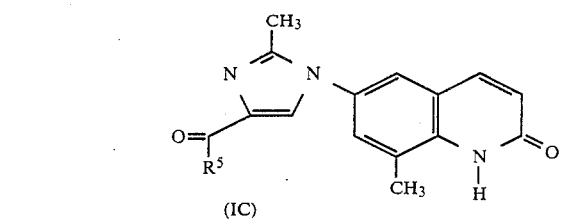

| Example No. | R⁵ | Form Isolated and m.p. (°C.) | Analysis % (Theoretical in brackets) | | |
|---|---|---|---|---|---|
| | | | C | H | N |
| 7 | —⟨phenyl⟩—O—CH₃ | Free base 0.25 H₂O, 310–3° | 69.7 (69.9 | 5.1 5.1 | 11.1 11.1) |
| 8 | —⟨phenyl⟩—F | Free base 0.25 H₂O, 288–90° | 69.0 (69.0 | 4.7 4.5 | 11.7 11.5) |

EXAMPLE 9

Preparation of 6-(4-[1-methyl-1,2,4-triazol-5-ylcarbonyl]-2-methylimidazol-1-yl)-8-methyl-2-(1H)-quinoline

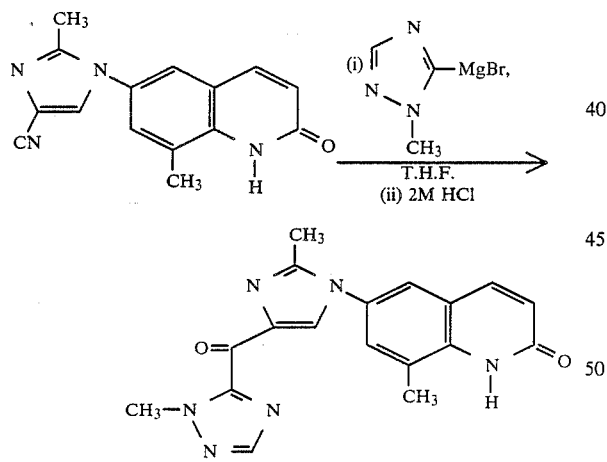

n-Butyllithium (4 cm³ of a 1.5M solution in diethyl ether) was added dropwise to a stirred solution of 1-methyl-1,2,4-triazole (0.50 g) in tetrahydrofuran (THF) (20 cm³) at −70° under nitrogen. After 15 minutes anhydrous magnesium bromide etherate (1.55 g) was added and the mixture was warmed to room temperature over 1 hour. 6-(4-Cyano-2-methylimidazol-1-yl)-8-methyl-2-(1H)-quinolone (0.26 g) was added and the mixture was heated under reflux for 4.5 hours. The cooled mixture was quenched with water (10 cm³) and then stirred for 30 minutes with 2M hydrochloric acid (10 cm³). The mixture was basified with 10% aqueous sodium carbonate solution to pH 10 (approximately) and extracted with ethyl acetate (3×100 cm³). The combined and dried (MgSO₄) organic extracts were evaporated in vacuo to give a solid which was chromatographed on silica (Merck "MK 60.9385" [Trade Mark]). Elution with methanol:chloroform, 1:50 by volume, followed by combination and evaporation of appropriate fractions, gave a solid which was boiled in ethyl acetate. Filtration afforded the title compound, m.p. 239°–4°, (0.05 g).

Analysis %: Found: C, 62.1; H, 4.7; N, 24.1; Calculated for C₁₈H₁₆N₆O₂: C, 62.1; H, 4.6; N, 24.1.

EXAMPLE 10

Preparation of 6-(5-acetyl-2,4-dimethylimidazol-1-yl)-8-methyl-2-(1H)-quinolone (Alternative to Example 2)

This compound was prepared similarly to Example 3 using 6-(5-cyano-2,4-dimethylimidazol-1-yl)-8-methyl-2-(1H)-quinolone and methyl magnesium bromide as the starting materials.

Analysis %: Found: C, 68.8; H, 5.7; N, 14.4; Calculated for C₁₇H₁₇N₃O₂: C, 69.2; H, 5.8; N, 14.2.

EXAMPLE 11

Preparation of 6-(4-[4-fluorophenyl]-2-methylimidazol-1-yl)-8-methyl-2-(1H)-quinolone, 0.25H₂O

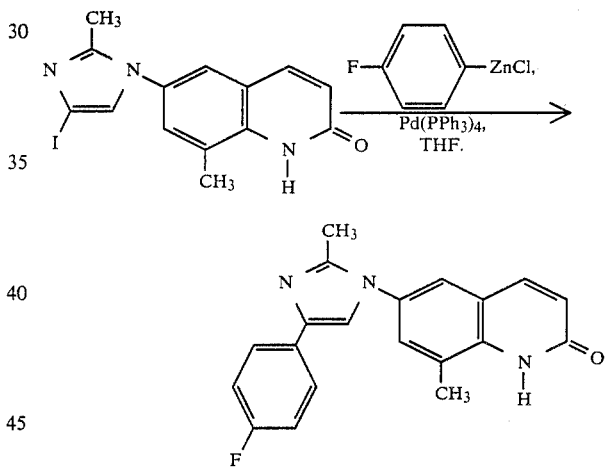

n-Butyllithium (3.5 cm³ of a 1.43M solution in n-hexane) was added dropwise to a stirred solution of 4-bromo-fluorobenzene (0.88 g) in tetrahydrofuran (THF) (20 cm³) at −70° under nitrogen. After 0.5 hours a solution of anhydrous zinc chloride (0.68 g) in THF (10 cm³) was added dropwise, and the mixture was warmed to room temperature over 1 hour. 6-(4-Iodo-2-methylimidazol-1-yl)-8-methyl-2-(1H)-quinolone (0.37 g) and tetrakis(triphenylphosphine)palladium (O) (0.01 g) were added and the mixture heated under reflux for 1.5 hours. The cooled solution was quenched with water (10 cm³) and poured into a saturated solution of ethylenediaminetetraacetic acid disodium salt in water (30 cm³), which had been adjusted to pH 9 by addition of sodium carbonate solution. This mixture was extracted with dichloromethane (3×100 cm³) and the combined and dried (MgSO₄) extracts were evaporated in vacuo to give a residue which was chromatographed on silica (Merck "MK 60.9385" [Trade Mark]) eluting with methanol:dichloromethane, 1:19 by volume. Collection and evaporation of appropriate fractions afforded a solid which was recrystallised from ethyl acetate to give the title compound, m.p. 289°–291° (0.14 g).

Analysis %: Found: C, 71.3; H, 5.0; N, 12.2; Calculated for C$_{20}$H$_{16}$N$_3$OF, 0.25H$_2$O: C, 71.2; H, 4.9; N, 12.4.

EXAMPLES 12–19

The following compounds (formula ID) were prepared similarly to the procedure of Example 11 using the appropriately substituted aryl zinc chloride, the appropriate iodoimidazole derivative and tetrakis(triphenylphosphine)palladium (O) as the starting materials:

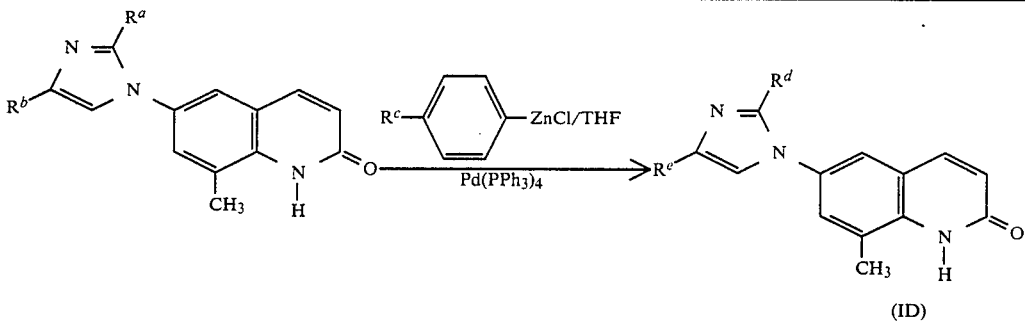

(ID)

| Example No. | $R^a$ | $R^b$ | $R^c$ | $R^d$ | $R^e$ | Form Isolated and m.p. (°C.) | Analysis % (Theoretical in brackets) C | H | N |
|---|---|---|---|---|---|---|---|---|---|
| 12 | —I | —CH$_3$ | —H | phenyl | —CH$_3$ | Free base 0.5 H$_2$O 293–295° | 74.1 (74.4 | 5.7 5.6 | 12.8 13.0) |
| 13 | —I | —CH$_3$ | —OCH$_3$ | 4-OCH$_3$-phenyl | —CH$_3$ | Free base 1.0 H$_2$O 265–266° | 69.9 (69.4 | 5.6 5.8 | 11.4 11.6) |
| 14 | —CH$_3$ | —I | —H | —CH$_3$ | phenyl | Free base 0.33 H$_2$O 280–282° | 74.9 (74.8 | 5.5 5.5 | 12.8 13.1) |
| 15 | —CH$_3$ | —I | —OCH$_3$ | —CH$_3$ | 4-OCH$_3$-phenyl | Free base 0.33 H$_2$O 278–281° | 71.8 (71.8 | 5.6 5.6 | 12.3 12.0) |
| 16 | CH$_3$ | I | —Cl | CH$_3$ | 4-Cl-phenyl | Free base 0.17 H$_2$O, 305–8° | 68.1 (68.1 | 4.6 4.6 | 11.7 11.9) |
| 17 | CH$_3$ | I | —CF$_3$ | CH$_3$ | 4-CF$_3$-phenyl | Free base 0.25 Et$_2$O, 282–4° | 65.5 (65.8 | 4.8 4.6 | 10.8 10.5) |
| 18 | CH$_3$ | I | —SCH$_3$ | CH$_3$ | 4-SCH$_3$-phenyl | Free base 0.25 H$_2$O, 291–3° | 68.8 (69.0 | 5.1 5.3 | 11.5 11.5) |
| 19 | CH$_3$ | I | —NHSO$_2$CH$_3$ | CH$_3$ | 4-NHSO$_2$CH$_3$-phenyl | Free base 0.5 H$_2$O, 313–6° | 60.7 (60.4 | 4.9 5.0 | 13.4 13.6) |

EXAMPLE 20

Preparation of
6-(4-[2,4-difluorophenyl]-2-methyl-imidazol-1-yl)-8-methyl-2-(1H)-quinolone, 0.5H₂O This compound, m.p. 262°–5°, was prepared similarly to Example 11 using 6-(4-iodo-2-methylimidazol-1-yl)-8-methyl-2-(1H)-quinolone, 2,4-difluorophenyl zinc chloride and tetrakis(triphenylphosphine)palladium (O) as the starting materials:

Analysis %: Found: C, 66.9; H, 4.2; N, 11.6; Calculated for C₂₀H₁₅F₂N₃O, 0.5H₂O: C, 66.7; H, 4.4; N, 11.7.

EXAMPLE 21

Preparation of
6-(4-[4-hydroxyphenyl]-2-methyl-imidazol-1-yl)-8-methyl-2-(1H)-quinolone.H₂O

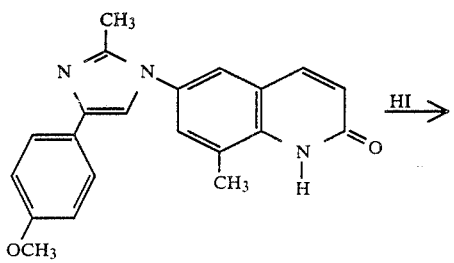

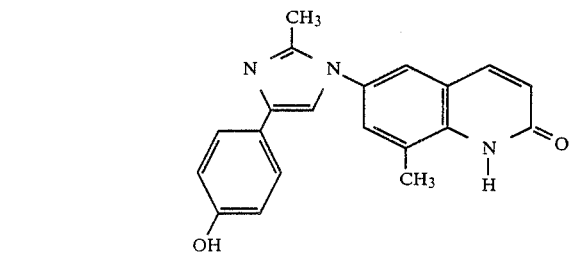

6-(4-[4-Methoxyphenyl]-2-methylimidazol-1-yl)-8-methyl-2-(1H)-quinolone (0.35 g) was added with stirring to 55% w/w hydroiodic acid (10 cm³) at room temperature (20°). The mixture was heated under reflux for 3 hours, cooled, poured into water (10 cm³), and basified to pH8 with sodium hydrogen carbonate solution. The crude product was filtered, washed with water, and then boiled in ethyl acetate/methanol to remove soluble organic impurities. The mixture was cooled and the solid filtered and dried to give the title compound, m.p. >380°, (0.24 g).

Analysis %: Found: C, 69.0; H, 5.1; N, 11.7; Calculated for C₂₀H₁₇N₃O₂, H₂O: C, 68.8; H, 5.4; N, 12.0.

EXAMPLE 22

Preparation of
6-(4-[4-methylsulphinylphenyl]-2-methyl-imidazol-1-yl)-8-methyl-2-(1H)-quinolone, 0.25H₂O

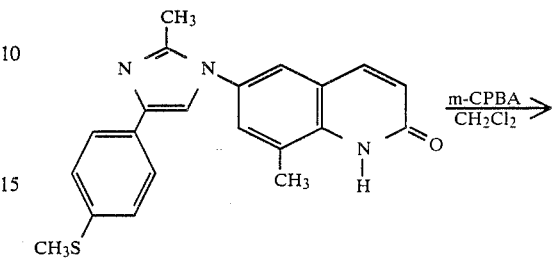

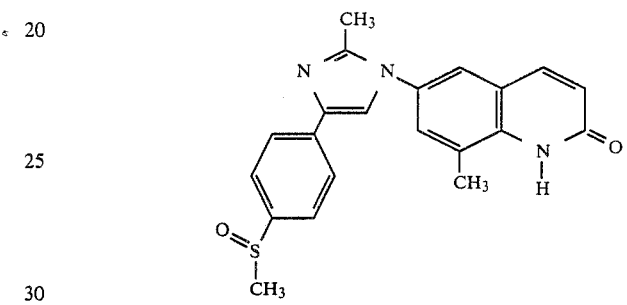

meta-Chloroperbenzoic acid (0.11 g) was added in portions over a period of 5 minutes to a stirred suspension of 6-(4-[4-methylthiophenyl]-2-methylimidazol-1-yl)-8-methyl-2-(1H)-quinolone (0.2 g) in dichloromethane (10 cm³) at 0°. The mixture was stirred at 0° for 30 minutes, then poured into saturated aqueous sodium carbonate solution (30 cm³) and extracted with dichloromethane (3×25 cm³). The combined and dried (MgSO₄) extracts were evaporated in vacuo to give a solid which was recrystallised from dichloromethane to give the title compound, m.p. 313°–5°, (0.08 g).

Analysis %: Found: C, 66.0; H, 4.9; N, 11.0; Calculated for C₂₁H₁₉N₃O₂S, 0.25H₂O: C, 66.1; H, 5.1; N, 11.0.

EXAMPLE 23

Preparation of
6-(4-[4-methylsulphonylphenyl]-2-methyl-imidazol-1-yl)-8-methyl-2-(1H)-quinolone

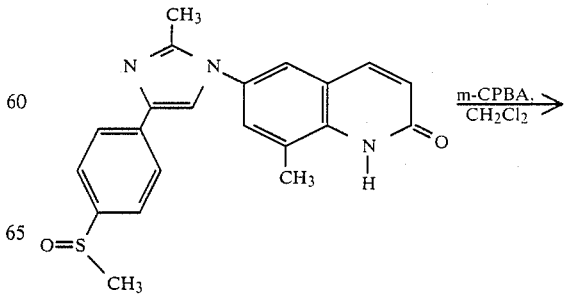

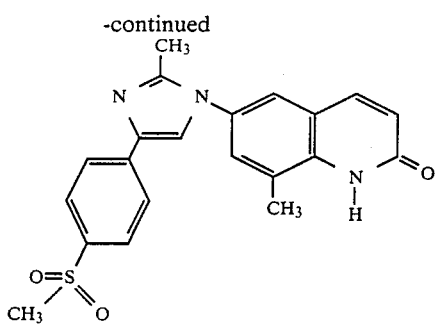

meta-Chloroperbenzoic acid (0.11 g) was added to a stirred solution of 6-(4-[4-methylsulphinylphenyl]-2-methyl-imidazol-1-yl)-8-methyl-2-(1H)-quinolone (0.14 g) in dichloromethane (20 cm$^3$) at room temperature. After 30 minutes the mixture was poured into saturated sodium carbonate solution (30 cm$^3$) and extracted with dichloromethane (3×30 cm$^3$). The combined and dried (MgSO$_4$) extracts were evaporated in vacuo to give a residue which was chromatographed on silica (Merck "MK 60.9385" [Trade Mark]) eluting with methanol:dichloromethane, 1:19 by volume. Collection and evaporation of appropriate fractions afforded a solid which was recrystallised from ethyl acetate to give the title compound, m.p. 345°–7° (0.06 g).

Analysis %: Found: C, 63.9; H, 5.0; N, 10.5; Calculated for C$_{21}$H$_{19}$N$_3$O$_3$S: C, 64.1; H, 4.8; N, 10.7.

EXAMPLE 24

(Alternative to Example 3)

Preparation of 6-(4-acetyl-2-methylimidazol-1-yl)-8-methyl-2-(1H)-quinolone, 0.25H$_2$O.

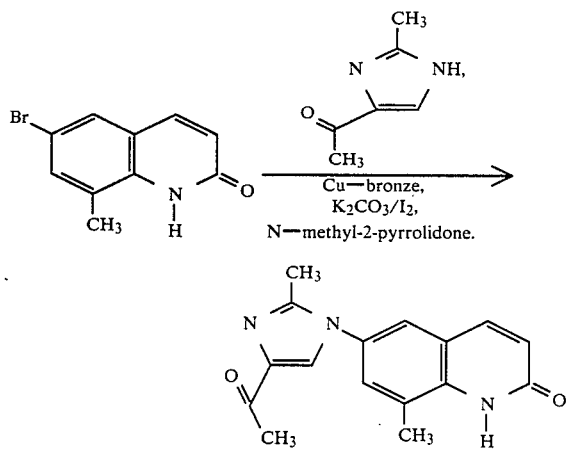

A mixture of 6-bromo-8-methyl-2-(1H)-quinolone (2.38 g), (see Preparation 67 of European patent application publication No. 0148623), 4-acetyl-2-methylimidazole (2.48 g), finely divided copper-bronze (0.64 g), potassium carbonate (1.38 g), and a few crystals of iodine was stirred and heated in N-methyl-2-pyrrolidone (8 cm$^3$) at 190° C. for 24 hours under nitrogen. The cooled mixture was then poured into methanol:dichloromethane (100 cm$^3$, 1:10 by volume), stirred and filtered. The filtrate was poured into aqueous ammonia (20 cm$^3$, S.G. 0.880) and the mixture was filtered through "Solkafloc" (Trademark for a cellulose-based filtering aid). The filtrate was separated and the aqueous phase was re-extracted with methanol:dichloromethane (3×100 cm$^3$, 1:10 by volume). The combined and dried (MgSO$_4$) organic extracts were evaporated in vacuo to give a residue which was chromatographed on silica (Merck "MK 60.9385" [Trademark]). Elution with methanol:dichloromethane, 1:33 by volume, followed by combination and evaporation of the appropriate fractions, gave unreacted starting bromo-quinolone (0.68 g) and a solid which was recrystallised from ethyl acetate/methanol to afford the title compound, m.p. 306°–8°, (0.26 g), which was also confirmed spectroscopically to be identical to the product of Example 3.

Analysis %: Found: C, 67.6; H, 5.7; N, 14.6; Calculated for C$_{16}$H$_{15}$N$_3$O$_2$, 0.25H$_2$O: C, 67.3; H, 5.5; N, 14.7.

The following Preparations, in which all temperatures are in °C., illustrate the preparation of certain starting materials used in the previous Examples:

PREPARATION 1

6-(2-Iodo-4-methylimidazol-1-yl)-8-methyl-2-(1H)-quinolone, 0.67 H$_2$O

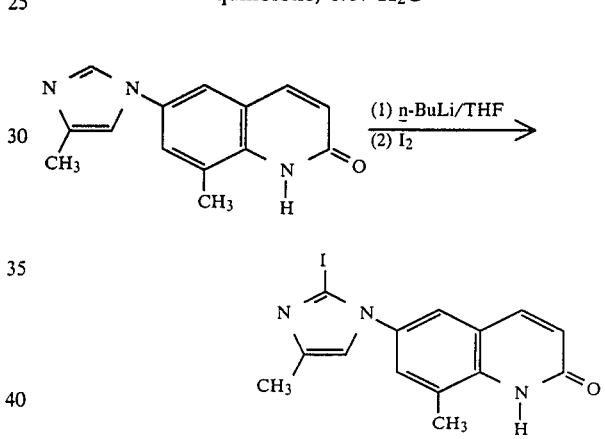

n-Butyllithium (2.94 cm$^3$ of a 1.43M solution in n-hexane) was added dropwise to a stirred suspension of 6-(4-methylimidazol-1-yl)-8-methyl-2-(1H)-quinolone (0.45 g) in tetrahydrofuran (THF) (25 cm$^3$) at −70° under nitrogen. After 30 minutes iodine (0.51 g) was added and the mixture was stirred for a further 30 minutes at −70° before warming to room temperature. The mixture was quenched with saturated ammonium chloride solution (10 cm$^3$), the THF evaporated in vacuo, and the residue partitioned between water (20 cm$^3$) and dichloromethane (50 cm$^3$). The aqueous phase was re-extracted with dichloromethane (2×50 cm$^3$), and the combined and dried (MgSO$_4$) organic extracts were evaporated in vacuo to give a residue which was chromatographed on silica (Merck "MK 60.9385" [Trade Mark]). Elution with chloroform, followed by combination and evaporation of the appropriate fractions, gave a solid which was recrystallised from ethyl acetate to afford the title compound, decomposition point 260° (0.27 g).

Analysis %: Found: C, 44.7; H, 3.6; N, 10.8; Calculated for C$_{14}$H$_{12}$N$_3$OI.0.67H$_2$O: C, 44.6; H, 3.5; N, 11.1.

PREPARATION 2

6-(4-Cyano-2-methylimidazol-1-yl)-8-methyl-2-(1H)-quinolone 0.67 H₂O

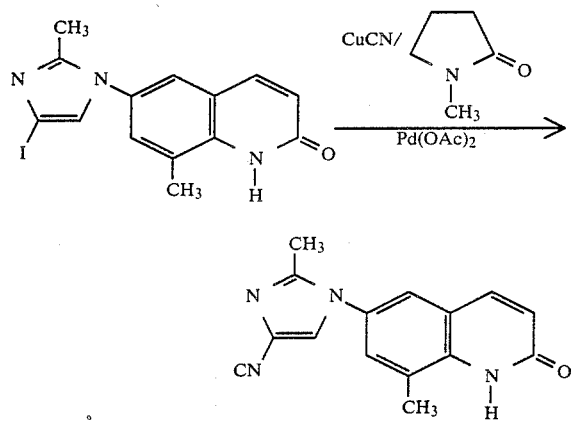

A mixture of 6-(4-Iodo-2-methylimidazol-1-yl)-8-methyl-2-(1H)-quinolone (0.55 g), cuprous cyanide (0.27 g) and palladium acetate (0.03 g) in 1-methyl-2-pyrrolidone (5 cm³) was heated and stirred at 175° for 2 hours. The cooled mixture was poured into aqueous ammonia solution (30 cm³; S.G. 0.880) and extracted with dichloromethane (3×100 cm³). The combined and dried (MgSO₄) organic extracts were filtered and evaporated in vacuo and the residue was chromatographed on silica (Merck "MK 60.9385" [Trade Mark]) eluting with chloroform. Combination and evaporation of the appropriate fractions afforded the title compound, m.p. >350°, (0.22 g).

Analysis %: Found: C, 65.3; H, 4.5; N, 20.1; Calculated for $C_{15}H_{12}N_4O$, $0.67H_2O$: C, 65.2; H, 4.8; N, 20.3.

PREPARATION 3

6-(5-Cyano-2,4-dimethylimidazol-1-yl)-8-methyl-2-(1H)-quinolone, 0.25 H₂O, m.p. 334°–337°, was prepared similarly to the previous Preparation using 6-(5-iodo-2,4-dimethylimidazol-1-yl)-8-methyl-2-(1H)-quinolone, cuprous cyanide and palladium acetate as the starting materials:

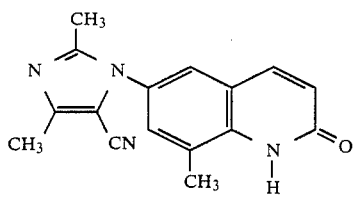

Analysis %: Found: C, 68.0; H, 5.1; N, 20.1; Calculated for $C_{16}H_{14}N_4O$, $0.25H_2O$: C, 68.0; H, 5.3; N, 19.8.

PREPARATIONS 4–6

The following compounds were prepared similarly to Example 1, using the appropriately substituted trans-3-ethoxy propenamide and 98% w/w $H_2SO_4$ as the starting materials:

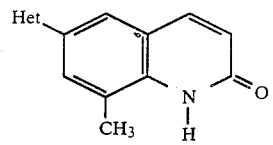

| Preparation No. | Het | Form Isolated and m.p. (°C.) | Analysis % (Theoretical in brackets) C | H | N |
|---|---|---|---|---|---|
| 4 | ![](CH₃, N=, I, N~) | Free base 0.33 H₂O 285–7° | 45.3 (45.3 | 3.3 3.4 | 11.3 11.3) |
| 5 | ![](N=, CH₃, N~) | Free base 292–5° | 69.8 (70.3 | 5.5 5.5 | 17.4 17.6) |
| 6 | ![](CH₃, N=, CH₃, N~) | Free base 322.5–325° | 71.4 (71.1 | 6.1 6.0 | 16.7 16.6) |

PREPARATION 7

Trans-1-[4-{N-(3-ethoxypropenamido)}-3-methylphenyl]-4-iodo-2-methylimidazole

A solution of trans-3-ethoxypropenoyl chloride (1.52 g) in tetrahydrofuran (THF) (25 cm³) was added dropwise to a stirred solution of 1-(4-amino-3-methylphenyl)-4-iodo-2-methylimidazole (2.94 g) in anhydrous pyridine (25 cm³), cooled to −40° C., and the mixture was warmed to room temperature over 2 hours. The reaction mixture was quenched with 10% sodium carbonate solution (5 cm³), poured into water (50 cm³) and extracted with dichloromethane (3×100 cm³). The combined and dried (MgSO₄) organic extracts were evaporated in vacuo, and the residue chromatographed on silica (Merck "MK 60.9385" [Trade Mark]) eluting with methanol:dichloromethane, 1:19 by volume. Combination and evaporation of the appropriate fractions gave a solid which was recrystallised from ethyl acetate to give the title compound, m.p. 172°–4°, (3.46 g).

Analysis %: Found: C, 46.8; H, 4.5; N, 10.1; Calculated for $C_{16}H_{18}N_3O_2I$: C, 46.7; H, 4.4; N, 10.2.

PREPARATIONS 8-11

The following compounds were prepared similarly to Preparation 7 using the appropriately substituted aniline and trans-3-ethoxypropenoyl chloride as the starting materials:

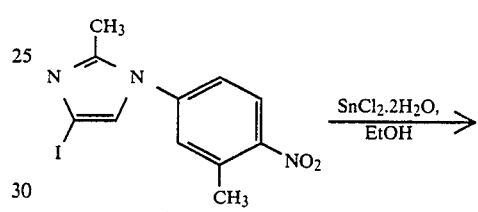

| Preparation No. | Het | Form Isolated and m.p. (°C.) | Analysis % (Theoretical in brackets) | | |
|---|---|---|---|---|---|
| | | | C | H | N |
| 8 | (imidazole with COCH₃, CH₃) | Free base, 189–191° | 65.9 (66.1 | 6.2 6.4 | 12.7 12.8) |
| 9 | (imidazole with CH₃) | Free base, 181–3° | 67.3 (67.3 | 6.8 6.7 | 14.6 14.7) |
| 10 | (imidazole with CH₃, CH₃) | Free base, 142.5–144.5° | 68.6 (68.2 | 7.1 7.1 | 13.9 14.0) |
| 11 | (imidazole with CH₃, CH₃, COCH₃) | Free base, crude oil | Characterised by ¹H N.M.R. | | |

PREPARATION 12

6-(5-Iodo-2,4-dimethylimidazol-1-yl)-8-methyl-2-(1H)-quinolone, 0.5 H₂O

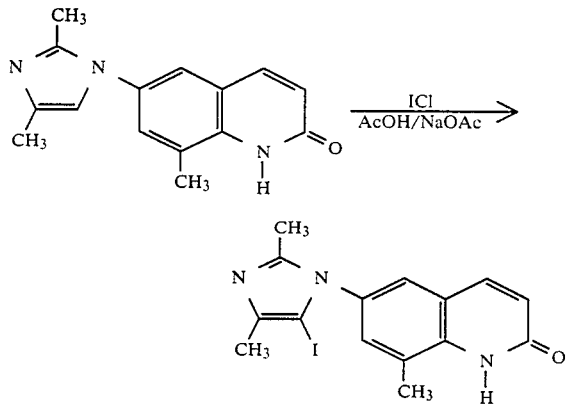

A solution of iodine monochloride (0.41 g) in acetic acid (5 cm³) was added dropwise to a stirred solution of 6-(2,4-dimethylimidazol-1-yl)-8-methyl-2-(1H)-quinolone (0.51 g) and sodium acetate (0.33 g) in acetic acid (10 cm³), and the mixture was stirred for 16 hours. The acetic acid was evaporated in vacuo, 10% sodium carbonate solution (50 cm³) was added, and the mixture extracted with dichloromethane (3×50 cm³). The combined and dried (MgSO₄) organic extracts were evaporated in vacuo and the residue chromatographed on silica (Merck "MK 60.9385" [Trade Mark]) eluting with ethyl acetate. Combination and evaporation of the appropriate fractions gave a solid which was recrystallised from methanol-ethyl acetate to afford the title compound, m.p. 242°–5°, (0.38 g).

Analysis %: Found: C, 46.4; H, 3.7; N, 11.0; Calculated for C₁₅H₁₄N₃OI, 0.5H₂O: C, 46.4; H, 3.9; N, 10.8.

PREPARATION 13

1-(4-Amino-3-methylphenyl)-4-iodo-2-methylimidazole

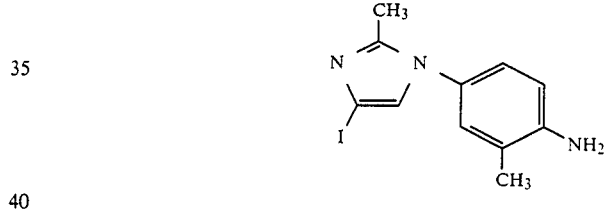

Stannous chloride dihydrate (9.04 g) was added portionwise to a stirred suspension of 4-Iodo-1-(3-methyl-4-nitrophenyl)-2-methylimidazole (2.75 g) in absolute ethanol (50 cm³) under nitrogen. After heating under reflux for 1 hour, the cooled mixture was basified to pH8 with aqueous 2.5M sodium hydroxide, and extracted with chloroform (3×100 cm³). The combined and dried (MgSO₄) organic extracts were evaporated in vacuo to give a residue which was chromatographed on silica (Merck "MK 60.9385" [Trade Mark]) eluting with methanol:dichloromethane, 1:25 by volume. Combination and evaporation of appropriate fractions afforded the title compound as a crude oil (2.41 g), which was used directly without further purification.

PREPARATIONS 14–16

The following compounds were prepared similarly to the previous Preparation using the appropriately substituted nitrobenzene derivative and stannous chloride dihydrate as the starting materials:

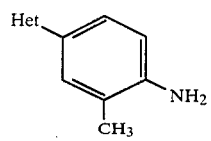

| Preparation No. | Het | Form Isolated and m.p. (°C.) | Analysis % (Theoretical in brackets) | | |
|---|---|---|---|---|---|
| | | | C | H | N |
| 14 | COCH₃ on imidazole (2-CH₃, N-) | Free base 0.17 H₂O, 157-9° | 67.3 (67.2 | 6.5 6.6 | 18.1 18.1) |
| 15 | 2-methyl imidazole | Free base, 109-111.5° | 70.5 (70.6 | 7.0 7.0 | 22.3 22.4) |
| 16 | 2,5-dimethyl imidazole | Free base, 92-6° | Characterised by ¹H N.M.R. | | |

PREPARATION 17

4-Iodo-1-(3-methyl-4-nitrophenyl)-2-methylimidazole

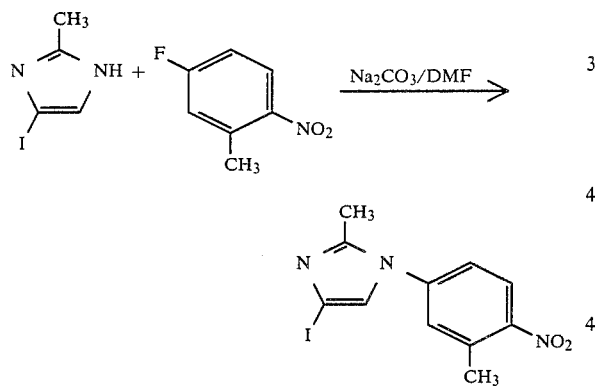

A mixture of 5-fluoro-2-nitrotoluene (7.9 g), 4-iodo-2-methylimidazole (9.0 g) and sodium carbonate (4.5 g) was heated with stirring in dimethylformamide (50 cm³) at 120° for 16 hours under nitrogen. The mixture was poured into water (50 cm³) and extracted with chloroform (3×100 cm³). The combined and dried (MgSO₄) organic extracts were concentrated in vacuo to give a solid which was chromatographed on silica (Merck "MK 60.9385" [Trade Mark]) eluting with ethyl acetate:toluene, 1:5 by volume. Combination and evaporation of appropriate fractions afforded a solid which was recrystallised from dichloromethane-hexane to give the title compound, m.p. 146°-8°, (4.0 g).

Analysis %: Found: C, 38.5; H, 3.1; N, 12.4; Calculated for C₁₁H₁₀N₃O₂I: C, 38.5; H, 2.9; N, 12.2.

PREPARATIONS 18-20

The following compounds were prepared similarly to the previous Preparation using 5-fluoro-2-nitro-toluene, the appropriately substituted imidazole, and sodium carbonate as the starting materials:

| Preparation No. | Het | Form Isolated and m.p. (°C.) | Analysis % (Theoretical in brackets) | | |
|---|---|---|---|---|---|
| | | | C | H | N |
| 18 | COCH₃ imidazole | Free base, 157-9° | 59.7 (60.2 | 5.1 5.0 | 16.3 16.2) |
| 19 | 2-methyl imidazole | Free base, 144-7° | 61.0 (60.8 | 5.1 5.1 | 19.6 19.3) |
| 20 | 2,5-dimethyl imidazole | Free base, 135.5-38° | 62.3 (62.0 | 5.7 5.7 | 18.2 17.9) |

PREPARATION 21

5-Acetyl-1-(4-amino-3-methylphenyl)-2,4-dimethylimidazole

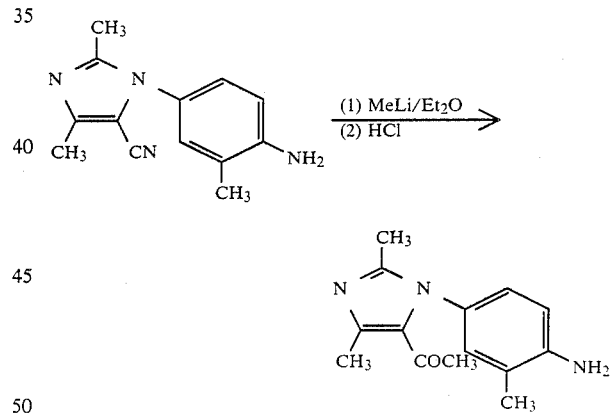

Methyllithium (219 cm³ of a 1.5M solution in ether) was added dropwise to a stirred suspension of 1-(4-amino-3-methylphenyl)-5-cyano-2,4-dimethylimidazole (9.3 g) in ether (100 cm³) at −70° under nitrogen. The mixture was allowed to warm to room temperature over 1 hour and then heated under reflux for 5 hours. The mixture was quenched by the dropwise addition of water (50 cm³), acidified with 2M hydrochloric acid (50 cm³), and warmed on a steam bath for 5 minutes. The mixture was basified with 10% sodium carbonate solution to pH9 and extracted with dichloromethane (3×200 cm³). The combined and dried (MgSO₄) organic extracts were evaporated in vacuo to give a residue which was chromatographed on silica (Merck "MK 60.9385" [Trade Mark]). Elution of the column with hexane:ethyl acetate, 1:1, gave firstly fractions containing recovered starting material (2.9 g). Further elution with hexane:ethyl acetate, 1:4, followed by combination and evaporation of the appropriate fractions, afforded the title compound as an oil (5.6 g), which was used (Preparation 11) without further purification.

PREPARATION 22

The following compound, m.p. 152°–155.5°, was prepared similarly to Preparation 2, using 1-(4-amino-3-methylphenyl)-5-iodo-2,4-dimethylimidazole and cuprous cyanide as the starting materials but without the use of a palladium acetate catalyst.

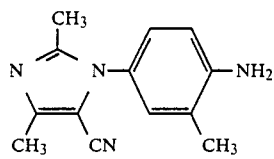

Analysis %: Found: C, 67.1; H, 6.1; N, 24.0; Calculated for $C_{13}H_{14}N_4$, 0.33$H_2O$: C, 67.2; H, 6.4; N, 24.1.

PREPARATION 23

1-(4-Amino-3-methylphenyl)-5-iodo-2,4-dimethylimidazole

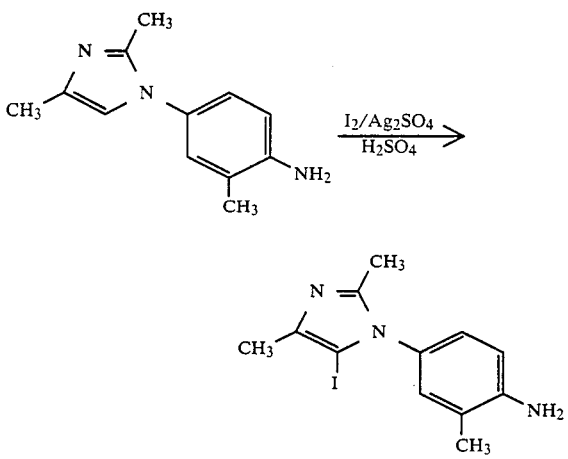

Silver sulphate (21.8 g) and crushed iodine (35.5 g) were added portionwise to a stirred solution of 1-(4-amino-3-methylphenyl)-2,4-dimethylimidazole (25.4 g) in sulphuric acid (100 cm³) cooled to −10°. After heating at 55° C. for 2 hours, the cooled mixture was poured onto ice (500 g). The mixture was cautiously adjusted to pH8 by addition of concentrated ammonia solution (S.G. 0.880) and extracted with chloroform (2×500 cm³). The organic extracts were combined, filtered through "Arbocel" (silica) [Trade Mark], and washed with saturated sodium thiosulphate solution (200 cm³). The organic solution was dried (MgSO₄) and evaporated in vacuo to give a residue which, on trituration with ether, gave the title compound (32.25 g) as a crude solid which was used without further purification in Preparation 22.

PREPARATION 24

4-Iodo-2-methylimidazole

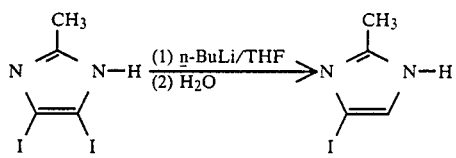

n-Butyllithium (86 cm³ of a 1.43M solution in n-hexane) was added dropwise to a stirred solution of 4,5-diiodo-2-methylimidazole (20.5 g) in tetrahydrofuran (THF) (300 cm³) at −70° under nitrogen. After 15 minutes water (20 cm³) was added, and the mixture warmed to room temperature over 1 hour. The mixture was evaporated in vacuo to low bulk, water (100 cm³) was added, and the pH adjusted to 8 by addition of 2M hydrochloric acid. The aqueous phase was extracted with dichloromethane (3×150 cm³), and the combined and dried (MgSO₄) organic extracts were evaporated in vacuo to give a residue which was chromatographed on silica (Merck "MK 60.9385" [Trade Mark]. Elution with ethyl acetate followed by combination and evaporation of the appropriate fractions gave 4-iodo-2-methylimidazole as a solid (9.0 g) which was characterised spectroscopically and used without further purification (Preparation 17).

PREPARATION 25

4,5-Diiodo-2-methylimidazole

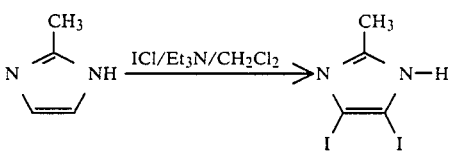

A solution of iodine monochloride (32.5 g) in dichloromethane (100 cm³) was added dropwise over 1.5 hours to a solution of 2-methylimidazole (8.2 g) and triethylamine (20.2 g) in dichloromethane (200 cm³) at −70° under nitrogen. The mixture was stirred for a further 30 minutes, warmed to −30°, and then poured into water (200 cm³). The resulting precipitate was filtered off, dried and recrystallised from ethyl acetate-hexane to afford 4,5-diiodo-2-methylimidazole (18.5 g) which was characterised spectroscopically and used directly without further purification (Preparation 24).

PREPARATION 26

2-Acetyl-4-methyl-imidazole

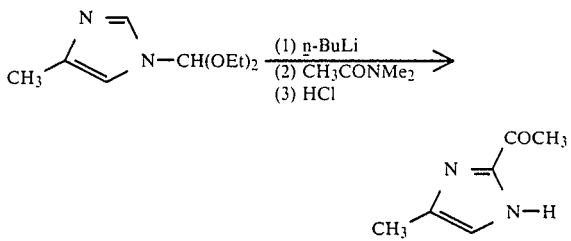

n-Butyllithium (7.7 cm³ of a 1.43M solution in n-hexane) was added dropwise to a stirred solution of 1,1-diethoxymethyl-4-methylimidazole (1.84 g) in tetrahydrofuran THF (50 cm³) at −40° under nitrogen. After 30 minutes N,N-dimethylacetamide (1.11 cm³) was added, the solution was warmed to room temperature, and stirred for 16 hours. The mixture was poured into 2M hydrochloric acid (50 cm³) and washed with dichloromethane (2×50 cm³). The aqueous phase was basified with 10% sodium carbonate solution and extracted with dichloromethane (4×40 cm³). The combined and dried (MgSO₄) organic extracts were evaporated in vacuo and the residue was chromatographed on silica (Merck "MK 60.9385" [Trade Mark]). Elution with ethyl acetate followed by combination and evaporation of the appropriate fractions gave 2-acetyl-4-methylimidazole, m.p. 113°–5°, (0.47 g).

Analysis %: Found: C, 58.1; H, 6.5; N, 22.8; Calculated for C₆H₈N₂O: C, 58.1; H, 6.5; N, 22.6.

PREPARATION 27

1-Diethoxymethyl-4-methylimidazole

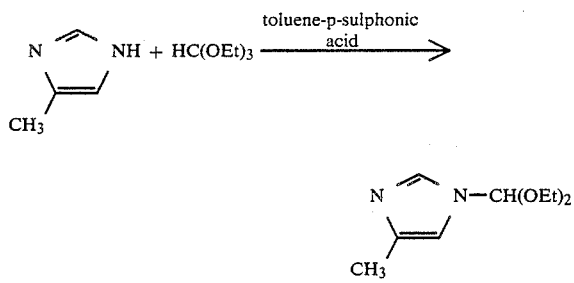

4-Methylimidazole (16.4 g), triethylorthoformate (118.4 g), and p-toluene sulphonic acid (1 g) were mixed and heated at 130° until evolution of ethanol ceased (approximately 2 hours). Volatile material was removed in vacuo and the residue was distilled under vacuum from anhydrous sodium carbonate (1 g) to afford the title compound, b.p. 126°–130°/5 mm (22.06 g). The product was characterised spectroscopically and used without further purification (Preparation 26).

PREPARATION 28

(Alternative to Preparation 2)

6-(4-Cyano-2-methylimidazol-1-yl)-8-methyl-2-(1H)-quinolone

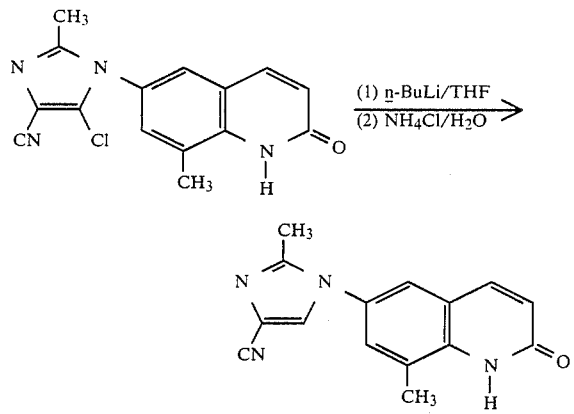

n-Butyllithium (17.5 cm³ of a 1.5M solution in n-hexane) was added dropwise to a stirred solution of 6-(5-chloro-4-cyano-2-methylimidazol-1-yl)-8-methyl-2-(1H)-quinolone (3.57 g) in tetrahydrofuran (THF) (100 cm³) at −70° under nitrogen. After 15 minutes saturated aqueous ammonium chloride solution (20 cm³) was added and the mixture was warmed to room temperature over 1 hour. The mixture was then poured into water (50 cm³), extracted with ethyl acetate (4×150 cm³), and the combined and dried (MgSO₄) organic extracts were evaporated in vacuo to give a residue which was chromatographed on silica (Merck "MK 60.9385" [Trade Mark]). Elution with methanol:dichloromethane, 1:19 by volume, followed by combination and evaporation of the appropriate fractions, gave a solid which was boiled with ethyl acetate/methanol, then filtered and dried to afford the title compound, (0.71 g), which was shown spectroscopically to be identical to the product of Preparation 2.

PREPARATION 29

6-(5-Chloro-4-cyano-2-methylimidazol-1-yl)-8-methyl-2-(1H)-quinolone

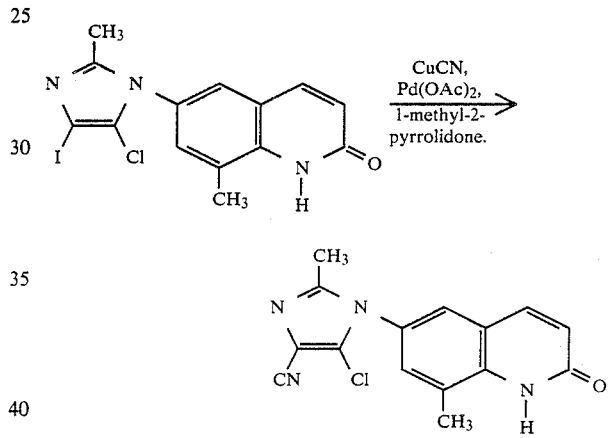

A mixture of 6-(5-chloro-4-iodo-2-methylimidazol-1-yl)-8-methyl-2-(1H)quinolone (1.0 g), cuprous cyanide (0.45 g) and palladium acetate (0.09 g) in 1-methyl-2-pyrrolidone (5 cm³) was stirred and heated at 160° for 4 hours. The cooled mixture was poured into aqueous ammonia solution (30 cm³; S.G. 0.880) and extracted with ethyl acetate (3×150 cm³). The combined and dried (MgSO₄) organic extracts were filtered and evaporated in vacuo and the residue was chromatographed on silica (Merck "MK 60.9385" [Trade Mark]) eluting with methanol:dichloromethane, 1:200 by volume. Combination and evaporation of the appropriate fractions afforded the title compound as a solid (0.54 g) which was characterised spectroscopically and used directly without further purification.

PREPARATION 30

6-(5-Chloro-4-iodo-2-methylimidazol-1-yl)-8-methyl-2-(1H)-quinolone, m.p. 288°–90°, was prepared similarly to Preparation 12 using 6-(5-chloro-2-methylimidazol-1-yl)-8-methyl-2-(1H)-quinolone, iodine monochloride, sodium acetate and acetic acid as the starting materials:

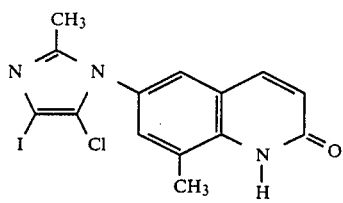

Analysis %: Found: C, 42.4; H, 2.9; N, 10.8; Calculated for $C_{14}H_{11}ClIN_3$: C, 42.1; H, 2.8; N, 10.5.

PREPARATION 31

6-(5-Chloro-2-methylimidazol-1-yl)-8-methyl-2-(1H)-quinolone, 0.25H₂O

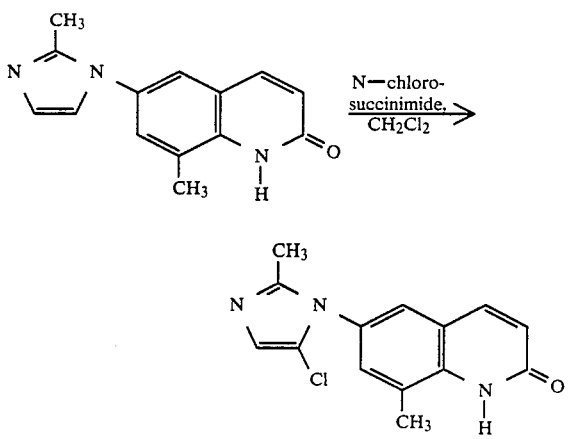

A mixture of 6-(2-methylimidazol-1-yl)-8-methyl-2-(1H)-quinolone (0.24 g) and N-chlorosuccinimide (0.14 g) in dichloromethane (10 cm³) was stirred at room temperature for 2 hours. The mixture was then chromatographed directly on silica (Merck "MK 60.9385" [Trade Mark]) eluting with methanol:dichloromethane, 1:20 by volume. Combination and evaporation of the appropriate fractions afforded the title compound, m.p. 258°–61°, (0.18 g).

Analysis %: Found: C, 60.4; H, 4.4; N, 15.1; Calculated for $C_{14}H_{12}ClN_3O$, 0.25H₂O: C, 60.4; H, 4.5; N, 15.1.

PREPARATION 32

6-(2-Methylimidazol-1-yl)-8-methyl-2-(1H)-quinolone (Alternative to Example 4 of European patent application publication No. 0166533.)

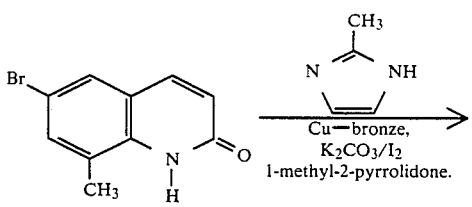

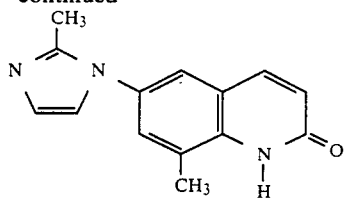

A mixture of 6-bromo-8-methyl-2-(1H)-quinolone (23.8 g), (see Preparation 67 of European patent application publication No. 0148623), 2-methylimidazole (16.4 g), copper bronze (6.4 g), potassium carbonate (13.8 g), and a few crystals of iodine was stirred and heated in 1-methyl-2-pyrrolidone (60 cm³) at 180° for 24 hours under nitrogen. The cooled mixture was poured into methanol:dichloromethane (500 cm³, 1:1 by volume), stirred and filtered through "Solkafloc" (Trademark for a cellulose-based filtering aid). The filtrate was poured into water (200 cm³), the organic phase separated, and the aqueous phase extracted with dichloromethane (6×250 cm³). The combined and dried (MgSO₄) organic extracts were evaporated in vacuo to give a residue which was chromatographed on silica (Merck "MK 60.9385" [Trade Mark]) eluting with methanol:dichloromethane, 1:11 by volume. Combination and evaporation of the appropriate fractions gave a residue which was recrystallised from methanol/ethyl acetate to afford a solid (14.9 g) which was confirmed spectroscopically to be identical to the product of Example 4 of European patent application publication No. 0166533. This solid was used directly without further purification.

PREPARATION 33

(Alternative to Preparation 4)

6-(4-Iodo-2-methylimidazol-1-yl)-8-methyl-2-(1H)-quinolone

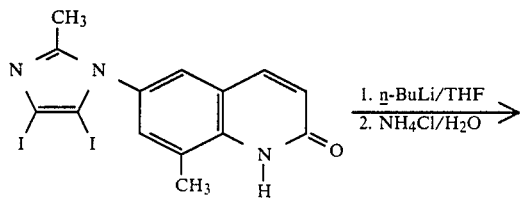

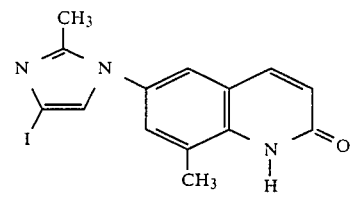

n-Butyllithium (16.42 cm³ of a 1.55M solution in n-hexane) was added dropwise to a stirred solution of 6-(4,5-di-iodo-2-methylimidazol-1-yl)-8-methyl-2-(1H)-quinolone (5.0 g) in tetrahydrofuran (100 cm³) at −30° under nitrogen. After 30 minutes saturated aqueous ammonium chloride solution (20 cm³) was added, and the mixture was warmed to room temperature. The mixture was then basified with saturated sodium carbonate solution to pH 10 (approximately) and extracted with methanol:ethyl acetate (1:19 by volume, 100 cm³)

and then methanol:dichloromethane (1:19 by volume, 2×200 cm³). The combined and dried (MgSO₄) organic extracts were evaporated in vacuo to give a residue which was chromatographed on silica (Merck "MK 60.9385" [Trade Mark]). Elution with methanol:dichloromethane, 1:19 by volume, followed by combination and evaporation of the appropriate fractions gave a solid which was recrystallised from methanol/ethyl acetate to afford the title compound, (0.87 g), which was shown spectroscopically to be identical to the product of Preparation 4. Also eluted were fractions which when combined and evaporated afforded a solid, (2.28 g), which was shown to be a mixture of the title compound, 6-(5-iodo-2-methylimidazol-1-yl)-8-methyl-2-(1H)-quinolone, and 6-(2-methylimidazol-1-yl)-8-methyl-2-(1H)-quinolone.

PREPARATION 34

6-(4,5-Di-iodo-2-methylimidazol-1-yl)-8-methyl-2-(1H)-quinolone, m.p. 274°–6°, was prepared similarly to Preparation 12 using 6-(2-methylimidazol-1-yl)-8-methyl-2-(1H)-quinolone (see Preparation 32), iodine monochloride, sodium acetate and acetic acid as the starting materials:

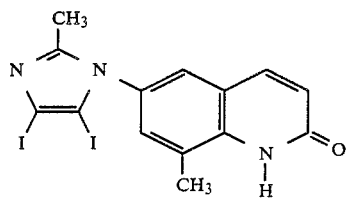

Analysis %: Found: C, 33.1; H, 2.4; N, 8.5; Calculated for C₁₄H₁₂I₂N₃O: H₂O: C, 33.0; H, 2.8; N, 8.3.

PREPARATION 35

(Alternative to Preparation 5)

6-(4-Methylimidazol-1-yl)-8-methyl-2-(1H)-quinolone was prepared similarly to Preparation 32 using 6-bromo-8-methyl-2-(1H)-quinolone (see Preparation 67 of European patent application publication No. 0148623), 4-methylimidazole, copper bronze, potassium carbonate and iodine as the starting materials. The product was confirmed spectroscopically to be identical to the product of Preparation 5.

We claim:

1. A substituted 2-(1H)-quinolone compound of the formula:

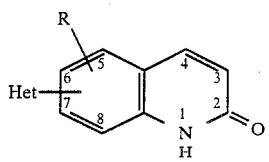

or a pharmaceutically acceptable salt thereof, wherein "Het" is is an imidazol-1-yl group attached by a nitrogen atom of said group to the 6-position of the quinolone ring, said imidazol-1-yl group being selectively substituted on the available ring carbon atoms with (a) one or two methyl groups and (b) a monosubstituent selected from —CO(C₁–C₄ alkyl), —COR¹, —COR² and —R¹ wherein R¹ is a phenyl group optionally substituted with one or two substituents each selected from C₁–C₄ alkyl, C₁–C₄ alkoxy, hydroxy, halo, trifluoromethyl, —NHSO₂(C₁–C₄ alkyl), —S(C₁–C₄ alkyl), —SO(C₁–C₄ alkyl) and —SO₂(C₁–C₄ alkyl), and R² is a triazolyl group attached by a ring carbon atom of said group to the adjacent carbonyl group, said triazolyl group being optionally substituted on the available ring carbon atoms with a C₁–C₄ alkyl group; and R is attached to the 8-position of the quinolone ring and is hydrogen, methyl, trifluoromethyl or bromo.

2. A compound as claimed in claim 1 wherein "Het" is an imidazol-1-yl group substituted with one or two methyl groups and a monoacetyl group.

3. A compound as claimed in claim 1 wherein R is methyl.

4. A compound as claimed in claim 1 wherein "Het" is a 2-acetyl-4-methylimidazol-1-yl, 4-acetyl-2-methylimidazol-1-yl or a 5-acetyl-2,4-dimethylimidazol-1-yl group, and R is methyl.

5. 6-(4-Acetyl-2-methylimidazol-1-yl)-8-methyl-2-(1H)-quinolone.

6. A pharmaceutical composition comprising a pharmaceutically acceptable carrier or diluent and an effective cardiac stimulating amount of a compound as claimed in claim 1.

7. A method for stimulating cardiac activity in the treatment of a subject afflicted with congestive heart failure, which comprises administering to said subject an effective cardiac stimulating amount of a compound as claimed in claim 1.

* * * * *